(12) United States Patent
Marchin et al.

(10) Patent No.: US 6,197,842 B1
(45) Date of Patent: Mar. 6, 2001

(54) MATERIAL BASED ON CROSSLINKED SILICONE POLYMER COMPRISING AN ATTACHED PHOTOINITIATOR, PROCESS FOR THE PREPARATION THEREOF, HYDROPHILIC POLYMERIC PRODUCT OBTAINED FROM THIS MATERIAL AND PROCESS FOR THE PREPARATION THEREOF, AND NOVEL PHOTOINITIATORS

(75) Inventors: Brigitte Marchin, Charenton-le-Pont; Dominique Baude, Saint-Ouen; Jean-Pierre Vairon, Bourg-la-Reine; Marine-Anne Dourges, Franconville; Philippe Chaumont, Lyons; Joël Steiner, Schiltigeim, all of (FR)

(73) Assignee: Essilor International Compagnie Generale d'Optique, Charenton Cedex (FR)

(*) Notice: Subject to any disclaimer, the term of this patent is extended or adjusted under 35 U.S.C. 154(b) by 0 days.

(21) Appl. No.: 09/202,844

(22) PCT Filed: Jun. 26, 1997

(86) PCT No.: PCT/FR97/01147

§ 371 Date: Dec. 18, 1998

§ 102(e) Date: Dec. 18, 1998

(87) PCT Pub. No.: WO97/49768

PCT Pub. Date: Dec. 31, 1997

(30) Foreign Application Priority Data

Jun. 27, 1996 (FR) .................................................. 96 08031

(51) Int. Cl.[7] ............................ C08G 77/38; C08L 83/04; C08L 83/10; G02C 7/04

(52) U.S. Cl. .................................. 522/35; 522/34; 522/80; 522/99; 522/148; 522/904; 522/905; 524/588; 525/903; 523/107

(58) Field of Search ....................................... 522/904, 905, 522/34, 35, 84, 85, 99, 80, 148; 524/588; 525/903; 523/107

(56) References Cited

U.S. PATENT DOCUMENTS

| | | |
|---|---|---|
| 4,362,895 | 12/1982 | Gupta et al. . |
| 4,534,838 | 8/1985 | Lin et al. . |
| 4,587,137 * | 5/1986 | Eckberg . |
| 4,587,276 * | 5/1986 | Lien et al. . |
| 4,666,953 * | 5/1987 | Klemarczyk et al. . |
| 4,795,766 | 1/1989 | Rutsch et al. . |
| 4,921,589 | 5/1990 | Yates et al. . |
| 5,100,689 * | 3/1992 | Goldberg et al. . |
| 5,147,901 | 9/1992 | Rutsch et al. . |

FOREIGN PATENT DOCUMENTS

| | | |
|---|---|---|
| 0 088 842 | 9/1983 | (EP) . |
| 0 108 037 | 9/1983 | (EP) . |
| 2073034 | 12/1970 | (FR) . |
| 2709756 | 9/1993 | (FR) . |

* cited by examiner

Primary Examiner—Susan W. Berman
(74) Attorney, Agent, or Firm—O'Keefe, Egan & Peterman

(57) ABSTRACT

This invention pertains to a process for the manufacture of a hydrophilic polymeric product, consisting in causing a material comprising a crosslinked silicone polymer matrix and photoinitiator groups dispersed and immobilized within the polymer matrix to swell in a swelling solution comprising a solvent for swelling the crosslinked silicone polymer of the matrix of the material, a photopolymerizable hydrophilic monomer and optionally a crosslinking agent and a proton- or electron-donating coinitiator compound, when the material comprises photoactivable photoinitiator groups and does not comprise proton- or electron-donating coinitiator groups causing the photopolymerizable hydrophilic monomer to diffuse into the swollen material, and polymerizing, by irradiation, the photopolymerizable hydrophilic monomer.

19 Claims, No Drawings

MATERIAL BASED ON CROSSLINKED SILICONE POLYMER COMPRISING AN ATTACHED PHOTOINITIATOR, PROCESS FOR THE PREPARATION THEREOF, HYDROPHILIC POLYMERIC PRODUCT OBTAINED FROM THIS MATERIAL AND PROCESS FOR THE PREPARATION THEREOF, AND NOVEL PHOTOINITIATORS

The present invention relates to a material based on crosslinked silicone polymer comprising a crosslinked silicone polymer matrix and photoinitiator groups which are dispersed and attached within the silicone matrix, and to a process for the preparation thereof.

The invention also relates to hydrophilic polymeric products obtained from the material based on silicone polymer, to a process for the preparation thereof and to the application thereof in the manufacture of hydrophilic contact lenses.

Finally, the invention relates to novel photoinitiators especially suited to being incorporated in the above material based on crosslinked silicone polymer and to the use of the process resulting in the hydrophilic polymeric products.

Materials based on silicone or polysiloxanes are well known for their very high permeability to oxygen, in particular polydimethylsiloxanes (PDMS). However, the use of pure polysiloxanes cannot be envisaged for the preparation of contact lenses because this material has the disadvantage of being hydrophobic and thus exhibits an absence of surface wettability which causes splitting of the lacrymal film. Furthermore, contact lenses made of pure silicone lead to suction effects (adhesion to the cornea of the eye).

Various techniques have already been provided in order to make silicone lenses compatible with the eye.

Some techniques are targeted at treating the surface of the lens in order to render it hydrophilic.

For example, a process for rendering contact lenses made of silicone hydrophilic at the surface is known in French Patent FR 2,073,034, which process consists in swelling the silicone matrix using a monomer of monoester or monoamide of acrylic or methacrylic acid type forming a hydrophilic polymer.

The contact lenses thus obtained exhibit a very low level of acrylic or methacrylic polymer incorporated at the surface of the silicone matrix.

Other techniques are targeted at obtaining hydrophilic materials of the interpenetrating polymer network (IPN) type from hydrophobic organosiloxane prepolymers and hydrophilic monomers of the monoester or monoamide of acrylic or methacrylic acid type. The material of IPN type is a material in which the hydrophobic prepolymers and the hydrophilic monomers are mixed together and react simultaneously in order to form two interwoven networks by an independent polymerization of the hydrophobic prepolymers and of the hydrophilic monomers, respectively.

This technique exhibits disadvantages because there are problems of solubility of the hydrophilic monomer in the hydrophobic prepolymer. It is thus difficult to obtain homogeneous materials and this technique is not suited to the production of materials with a high concentration of hydrophilic polymer and thus with high contents of water in the final material.

French Patent FR 2,709,756, on behalf of the Applicant Company, discloses a process for producing a hydrophilic silicone material of IPN type consisting, in a first stage, in swelling a polymer of PDMS type in a composition comprising acrylic acid, a photoinitiator, a crosslinking agent and a solvent for swelling the PDMS polymer and in then bringing about the polymerization of the acrylic acid by subjecting the swollen PDMS polymer to UV irradiation. It is thus possible to obtain materials which are hydrophilic to the core, with high levels of hydrophilicity. Although this process gives satisfactory results, it can still be improved, however. In particular, there exists a possibility of heterogeneity in the photoinitiator/hydrophilic monomer distribution within the matrix, insofar as these compounds diffuse at different rates, which can result in physical and mechanical heterogeneities.

Moreover, it would be desirable further to increase the level of hydrophilicity of the final material.

Finally, it is also desirable to simplify the implementation of the process disclosed in French Patent FR 2,709,756, for its industrial exploitation and for its application to the manufacture of contact lenses.

In order to solve these technical problems, the preparation has been carried out of a material based on crosslinked silicone polymer comprising a crosslinked silicone polymer matrix, that is to say in which the polymer network is three-dimensional, the distinguishing feature of which is to comprise photoinitiator groups which are dispersed and immobilized within the silicone matrix.

The processes for the subsequent treatment of this material based on crosslinked silicone polymer, which are targeted at rendering it hydrophilic to the core, are greatly simplified thereby and the hydrophilic products obtained exhibit particularly interesting and advantageous characteristics.

The material based on crosslinked silicone polymer comprising immobilized initiator groups and the process for the preparation thereof will now be described in more detail.

According to the invention, the crosslinked silicone matrix comprises photoinitiator groups or fragments distributed homogeneously throughout its volume and to the very heart of the matrix.

The photoinitiator groups can be attached by the following techniques:

According to a first technique, the photonitiator groups are attached to the silicone matrix ia a covalent chemical bond.

To this end, a photoinitiator functionalized by an SiH silyl group or by an unsaturated C=C double bond is prepared.

This double bond can be of vinyl, (meth)acrylic or allyl type.

The photoinitiator compound is introduced into a crosslinkable liquid composition comprising:

an oil A of a polysiloxane monomer or oligomer carrying Si-vinyl groups;

an oil B of a polysiloxane monomer or oligomer carrying Si—H groups;

a metal catalyst for the hydrosilylation reaction.

During the crosslinking by a hydrosilylation reaction carried out by the thermal route, the photoinitiator compound is grafted to the polysiloxane network via an Si—C covalent bond.

According to a second immobilization technique, use is made of a long-chain photoinitiator compound. This chain is preferably a polysiloxane chain on which the photoinitiator group(s) is (are) grafted. This photoinitiator compound is, in the same way as in the preceding technique, introduced into the liquid mixture of the polysiloxane precursors.

During the crosslinking of the mixture, the polysiloxane chain of the photoinitiator compound is physically immobilized within the crosslinked silicone polymer matrix obtained.

In this case, in contrast to the preceding technique, there is no chemical bond between the photoinitiator compound and the silicone matrix but a simple retention of physical nature, due in particular to the three-dimensional character of the network of the crosslinked silicone polymer of the matrix.

However, whatever the immobilization technique used, the photoinitiator groups remain attached in the polysiloxane matrix, even when the latter is subjected to extraction treatments with solvents. In other words, it is impossible to separate the photoinitiator groups from the matrix by extraction with solvents, whether these groups are grafted to the polymer forming the matrix or simply grafted to a long-chain compound physically immobilized within the matrix.

Thus, at the end of the hydrosilylation reaction, there is obtained a material based on crosslinked silicone polymer comprising a crosslinked silicone polymer matrix, in which matrix are distributed photoinitiator groups capable of generating free radicals by light irradiation.

The liquid silicone compositions used to produce the silicone polymer matrix are preferably polydimethylsiloxane oils with two constituents, the essential constituent units of which are represented below:

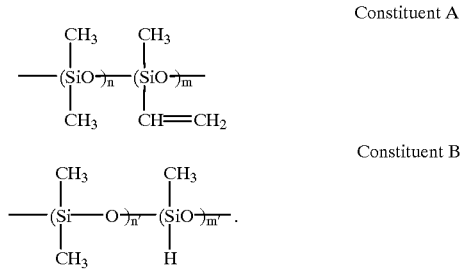

These silicone oils are crosslinked by virtue of a hydrosilylation catalyst. Such catalysts are well known to the person skilled in the art.

They are, for example, platinum, hexachloroplatinic acid, platinum-hydrocarbon complexes and rhodium complexes.

Platinum-based catalysts are generally used at concentrations of 10 ppm to 500 ppm, preferably of 50 to 300 ppm.

The reaction temperatures vary from room temperature to 250° C. according to the concentration and the type of catalyst used. The preferred temperatures vary from 50° C. to 150° C.

The constituents A and B are used in proportions such that their mixture includes from 0.8 to 1.9 SiH bonds per 1 Si-vinyl bond.

The polydimethylsiloxane (PDMS) polymer is preferably prepared by mixing two siloxane prepolymers developed by Rhone-Poulenc under the reference RTV 141 A and B and the functionalized photoinitiator in the desired proportions.

The oil A is composed of mono- and divinyl PDMS and of a platinum catalyst. This part comprises approximately $3.10 \times 10^{-4}$ vinyl functional groups per gram of RTV 141 A and its number-average molecular mass is 31,200.

The oil B is preferably a hydromethyl PDMS and comprises $4.07 \times 10^{-3}$ SiH functional groups per gram of RTV 141 B and its number-average molecular mass is 1770.

In order to obtain the polymer, 10 parts by weight of oil A and 1 part by weight of oil B and the photoinitiator are mixed and then the crosslinking is carried out as mentioned above.

The photoiniators, by means of which the photoinitiator groups can be introduced into the crosslinkable liquid compositions described above, will now be described in more detail.

The photoinitiator compounds comprise, on the one hand, a functional group intended to react with the SiH or Si-vinyl groups of the PDMS oils and, on the other hand, a photoinitiator group.

Such compounds can be obtained by functionalizing conventional photoinitiators, namely: any compound which produces free radicals under irradiation, whether by itself or by interaction with another proton- or electron-donating compound. That is to say that the photoinitiators used, or photopolymerization initiators, can equally well be of photocleavable type as of photoactivable type, with, however, a preference for those which are active in initiating the photopolymerization of the monomer for irradiation wavelengths lying in the UV region.

A photocleavable photoinitiator comprises one or more compounds which function by directly generating one or more polymerization-initiating free radicals, whereas a photoactivable photoinitiator is formed of a system producing such radicals by photoassisted oxidation/reduction reaction between a light-absorbing compound and a hydrogen or electron donor, both present in the system. Of course, mixtures of the two types of photoinitiators can also be used.

Examples of photocleavable compounds known per se are chosen from alkoxyacetophenone derivatives, benzoin ethers, phosphine oxides or benzoyloxime derivatives. Examples of known photoactivable photoinitiators comprise an absorber which produces free radicals, chosen from benzophenones, benzyls, xanthones, anthrones, thioxanthones, fluorenones, suberones or acridones, in combination with, as proton donor, a compound of the type of ethers, alcohols, amines or amino acids, or organometallic compounds.

Such photoinitiators can be functionalized by techniques known to the person skilled in the art.

Reference may usefully be made to the teaching of the following documents:

U.S. Pat. No. 4,507,187, which describes the manufacture of a photoiniator of aryoyl [sic] formate type functionalized by alkene or acetylene groups;

U.S. Pat. No. 4,477,326 and U.S. Pat. No. 4,587,276, which describe the production of photoinitiators of benzoin type functionalized by allyl groups;

U.S. Pat. No. 4,536,265, which describes the production of acetophenones with olefinic or acetylenic functionality; and the document "Photoinitiator with functional group", J.M.S.—Pure Appl—Chem [sic] A 31 (3) pp 305–318 (1994)—Kolar, Grube and Greber, which describes photoinitiators functionalized by a silyl group, namely 2-hydroxy-(or 2-methoxy)-2-methyl-1-[(4-dimethylsilyl)phenyl]propane-1-one [sic].

Among the photoinitiators of use in the present invention, those corresponding to the formula:

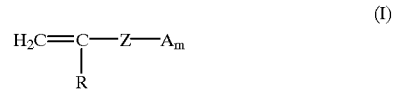

(I)

in which:

R represents a hydrogen atom or a methyl group,

Z is a divalent hydrocarbon-comprising chain comprising from 1 to 10 carbon atoms which can be interrupted by 1 to 3 atoms chosen from —O—, or

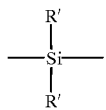

where R' is independently a hydrogen atom or an alkyl group, preferably a $C_1$–$C_6$ alkyl group and better still a methyl group, and $A_m$ is a group comprising a

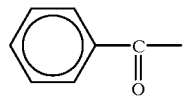

functional group, are more particularly recommended.

Z preferably represents the following divalent chains:

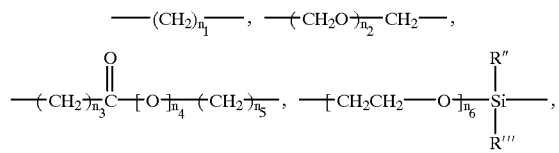

in which R" and R"' represent, independently of one another, an alkyl group, preferably a $C_1$–$C_6$ alkyl group and in particular a methyl group, $n_1$ and $n_2$ are integers from 1 to 6, $n_3$ and $n_5$ are integers from 0 to 4, $n_4$ is equal to 0 or 1, and $n_6$ is an integer from 0 to 5.

The $A_m$ group is preferably chosen from the groups corresponding to the formulae:

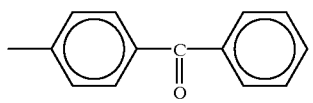
(II)

provided that Z comprises at least two carbon atoms;

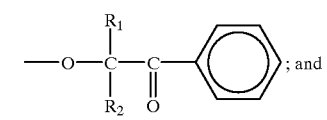
(III)
; and

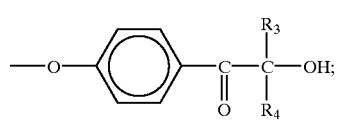
(IV)

in which $R_1$, $R_2$, $R_3$ and $R_4$, which are identical or different, are chosen from hydrogen and alkyl groups having from 1 to 6 carbon atoms, preferably a methyl group.

Other photoinitiators of use in the present invention correspond to the following formulae:

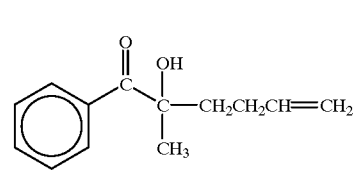
(Va)

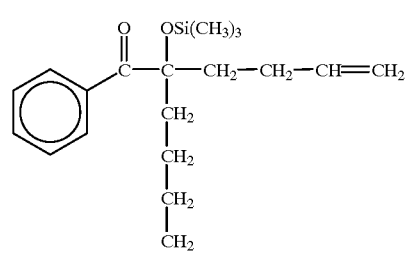
(Vb)

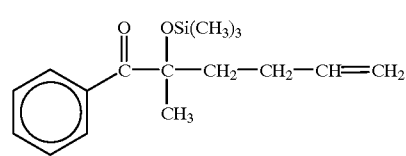
(Vc)

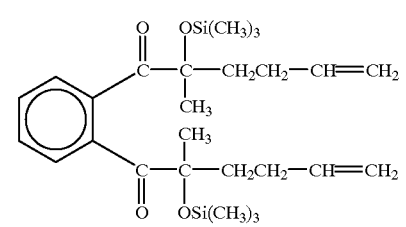
(Vd)

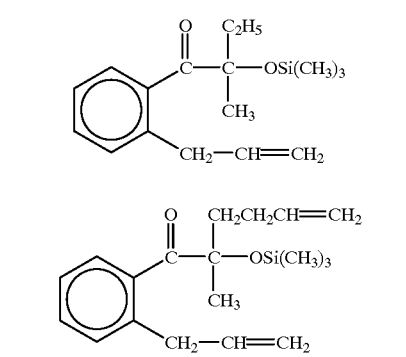
(Ve)

(Vf)

The photoinitiators corresponding to the above formula (I) and for which the $A_m$ group is chosen from the groups of formulae (II) to (IV) are novel, as well as the compounds of formulae (Vb) to (Vf).

The present invention thus also relates to these novel photoinitiators especially suited to being incorporated in the material based on crosslinked silicone polymer according to the invention and to the use of the process resulting in the hydrophilic polymeric products of the present invention.

The photoinitiators preferably correspond to one of the following formulae:

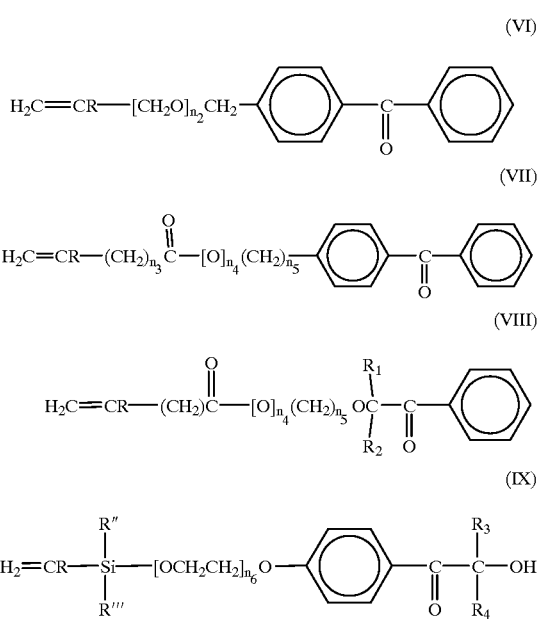

in which R, R", R"', $R^1$, $R^2$, $R^3$, $R^4$, $n_2$, $n_3$, $n_4$, $n_5$ and $n_6$ have the same meanings as above.

The photoinitiators preferably used in the context of the invention are:

4-allylbenzophenone (ALBP)

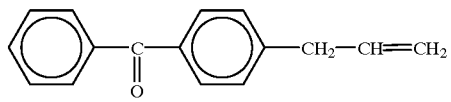

4-(allyloxymethyl)benzophenone (ALOBP)

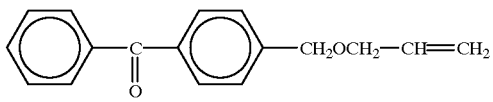

Such photoinitiators are introduced as mentioned above into the mixture of the siloxane prepolymers in a proportion of more than 0.1% by weight, preferably 0.5 to 10% by weight and better still from 0.5 to 4% by weight.

The photoinitiator will thus be attached by covalent bonding to the final silicone.

It is also possible to use long-chain photoinitiators obtained by reacting one of the photoinitiators mentioned above with a polysiloxane oil, preferably with a linear chain, by hydrosilylation reaction. The polysiloxane oil is preferably a PDMS oil with a molecular mass of between 132 and 50,000 g/mol, preferably between 250 and 10,000 g/mol.

The preparation of such photoinitiators is described in the article by Kolar, Grube and Greber mentioned above, as well as in the article "Functional polysiloxanes with benzophenone side groups: a photochemical application as radical polymerisation macroinitiators", Lydie Pouliquen, Xavier Coqueret, Alain Lablache-Combier and Claude Loucheux, Makromol. Chem., 113, 1273–1282 (1992).

The long-chain photoinitiator is introduced into the PDMS oil at a concentration such that the fraction by weight of the photoinitiating functional groups is equal to that: used for the conventional photoinitiators, typically from 0.05 to 5% by weight of photoinitiator functional groups, preferably from 0.05 to 2% by weight. When use is made of photoactivable photoinitiators, the hydrogen- or electron-donating compound can be introduced into the swelling solution used in the first stage of the hydrophilization process.

The donating compound can also be attached to the network of the PDMS matrix, that is to say introduced into the mixture of the siloxane prepolymers, insofar as the donating compound has been functionalized beforehand.

In this case, the donating compound will be attached to the network of the silicone matrix via a covalent bond.

This functionalized donating compound can also be fixed to a polysiloxane chain by hydrosilylation reaction and a donating compound with a long polysiloxane chain, preferably a PDMS chain, can thus be obtained which, introduced into the mixture of the siloxane prepolymers, will be physically retained in the final silicone matrix. The same polysiloxane oil is used for the preparation of the donating compound with a long polysiloxane chain as that defined for the preparation of the photoinitiator compound with a long polysiloxane chain.

One example of donating compound or coinitiator is ethyl 4-(dimethylamino)benzoate (EDMAB)

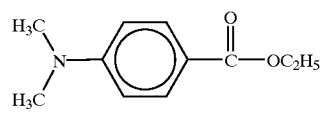

One functionalized coinitiator which can be used is 4-dimethylvinylsilane-N,N-dimethylaniline [sic].

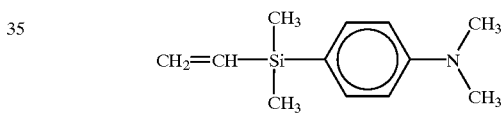

The amount of coinitiator used is generally a function of the amount of photoinitiator used. Use is made of concentrations of coinitiating units chosen within the same concentration ranges as the photoinitiators.

The novel photoinitiators according to the invention can be prepared by conventional processes well known to the person skilled in the art.

Examples of the preparation of photoinitiators according to the invention have been shown below.

Synthesis of

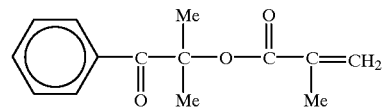

(Darocur® methacrylate)

20 g (0.122 mol) of Darocur® 1173

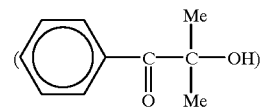

are introduced into a 250 ml, three-necked, round-bottomed flask equipped with a thermometer, a nitrogen inlet and a dropping funnel. 250 ml of ether, distilled once over sodium, and 20.4 ml (0.146 g) of distilled triethylamine are added. After purging with argon, methacrylic acid chloride is added dropwise with stirring. The temperature of the reaction medium increases and cooling is carried out from time to time by means of a cold water bath. The reaction medium immediately turns cloudy, the opacity increasing in step with the addition, and increases further after the end of the addition of the acid chloride. Once all the acid chloride has been added (13.1 ml, 0.134 mol), the reaction mixture is left stirring at room temperature for 2 hours. The mixture obtained is subsequently washed with 100 ml of water to which a few milliliters of HCl have been added, then with 100 ml of water and finally with 100 ml of water to which a few grams of $NaHCO_3$ have been added. The product obtained is dried over $MgSO_4$, filtered and evaporated to dryness to produce 23.5 g of expected product (Yield: 83%).

The product obtained is Darocur® methacrylate of formula:

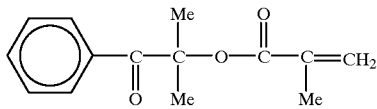

Synthesis of

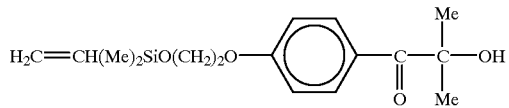

(Irgacure® vinylsilane or IVS)

150 ml of anhydrous tetrahydrofuran (THF) and 9.37 g ($4.18 \times 10^{-2}$ mol) of Irgacure® 2959

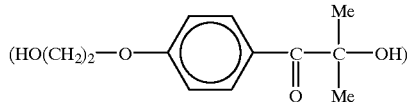

are introduced into a 500 ml, multi-neck, round-bottomed flask which is purged with argon and equipped with a dropping funnel for THF, a thermometer, an argon inlet, a dropping funnel for triethylamine (TEA) and a dropping funnel for chlorovinyldimethylsilane. The Irgacure® 2959 rapidly dissolves. 3.82 ml of TEA, distilled over $CaH_2$, are then added and, finally, the chlorovinyldimethylsilane is added dropwise. The temperature of the reaction mixture rises and it is cooled by means of an ice bath. A cream-white precipitate is immediately formed. At the end of the addition of the chlorovinyldimethylsilane [sic] (5.04 g, $4.18 \times 10^{-2}$ mol), the reaction mixture is left stirring for 4 hours. The solution obtained is filtered on sintered glass (porosity 4). The THF is driven off from the filtered product and the residue is taken up in cyclohexane. The mixture becomes cloudy, which cloudiness is removed by filtration. The solvent is then driven off in order to collect 12.44 g of a yellow oil. After distillation under reduced pressure at 175° C., two fractions of 5.13 g and 3.27 g respectively of the expected product are collected, i.e. a yield of 65%.

The product obtained is Irgacure® vinylsilane of formula:

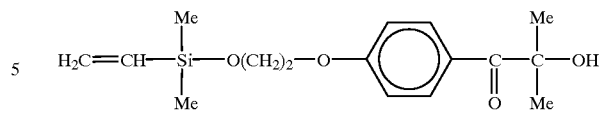

Synthesis of

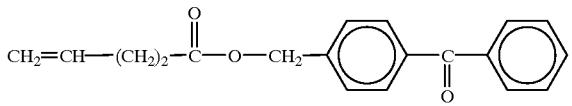

(3-butene-4-acyloxymethylbenzophenone)

a. Preparation of 4-(bromomethyl)benzophenone

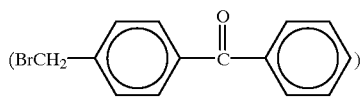

30 g (0.153 mol) of 4-methylbenzophenone are introduced into a 250 ml three-necked flask equipped with a reflux condenser and a dropping funnel containing 8.7 ml (0.168 mol) of bromine. In a first step, the reaction medium is heated to 70° C. and then, after complete dissolution of the solid, to 150° C. The bromine is then added dropwise over a period of 3 hours. The reaction is exothermic. The initially colorless solution becomes orange-yellow. Heating is maintained at 150° C. for 15 hours. At the end of the reaction, the temperature of the reaction medium is allowed to return to room temperature. The solution is brown in color. 75 ml of benzene and 35 ml of diethyl ether are added. Washing is carried out with a saturated $Na_2CO_3$ solution, then with a saturated $Na_2S_2O_3$ solution and finally with a saturated NaCl solution, in order to remove the salts formed and to bring the solution to a pH of the order of 6–7. The organic phase is recovered and the solvents are evaporated. A caramel-colored paste is obtained. It is recrystallized from 100 ml of ethanol. The cream-colored crystals are collected and dried under vacuum. The mother liquors are collected and a second crystallization is carried out. The crystals obtained are dried under vacuum. The yield of expected product is 50%, m=20.81 g.

b. Synthesis of 4-hydroxymethylbenzophenone:

The 4-bromomethylbenzophenone obtained in the preceding stage (2 g, 7.27 mmol) is introduced into a three-necked flask equipped with a reflux condenser and with magnetic stirring. A 15% by volume solution of water and of N-methyl-2-pyrrolidone (5.6/31.5 ml) is prepared in an Erlenmeyer flask. Slight warming is observed. This solution is subsequently introduced into a dropping funnel and it is added dropwise over 1 h 45 to the 4-bromomethylbenzophenone while heating the reaction medium to 80° C. At the end of the addition, the temperature of the solution is gradually raised to 110° C. Heating is maintained for 18 hours. At the end of the reaction, the temperature of the reaction medium returns to room temperature. 70 ml of water are added and the reaction medium becomes white after mixing. The organic phase is extracted three times with 70 ml of diethyl ether. The organic phases are then combined, washed 3 times with 150 ml of water and dried over $MgSO_4$. After evaporating the solvents on a rotary evaporator, 1.43 g of crude product are obtained (crude yield=93%).

Purification is carried out by distillation in a bulb oven. 1.16 g of the expected product are then obtained (final yield=75%).

c. Condensation of 4-hydroxymethylbenzophenone with 4-pentenoic [sic] acid chloride:

4-Pentenoic [sic] acid chloride (0.77 g, 6.5 mmol) and 4-hydroxymethylbenzophenone (1.16 g, 5.5 mmol) are introduced into 20 ml of anhydrous THF in a round-bottomed flask. Pyridine (0.56 g, 7 mmol) is added dropwise. A white precipitate is formed in step with the addition (pyridinium salt). The reaction is continued for 3 hours with magnetic stirring. At the end of the reaction, the salt is filtered off and washed with ether. The filtrate is then recovered and water is added. The aqueous phase is washed and then extracted 3 times with 30 ml of ether. The organic phases are combined, an aqueous $K_2CO_3$ solution is added and the organic phase is brought back to neutrality by addition of a saturated aqueous NaCl solution. Drying is subsequently carried out over $MgSO_4$ and the solvents are removed. 1.28 g of the expected product are obtained (yield=79%).

The photoinitiator compound obtained corresponds to the formula:

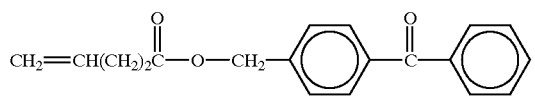

Synthesis of 4-allylbenzophenone (ALBP)

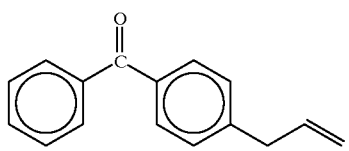

The scheme for the preparation of allylbenzophenone is shown below.

Synthetic scheme

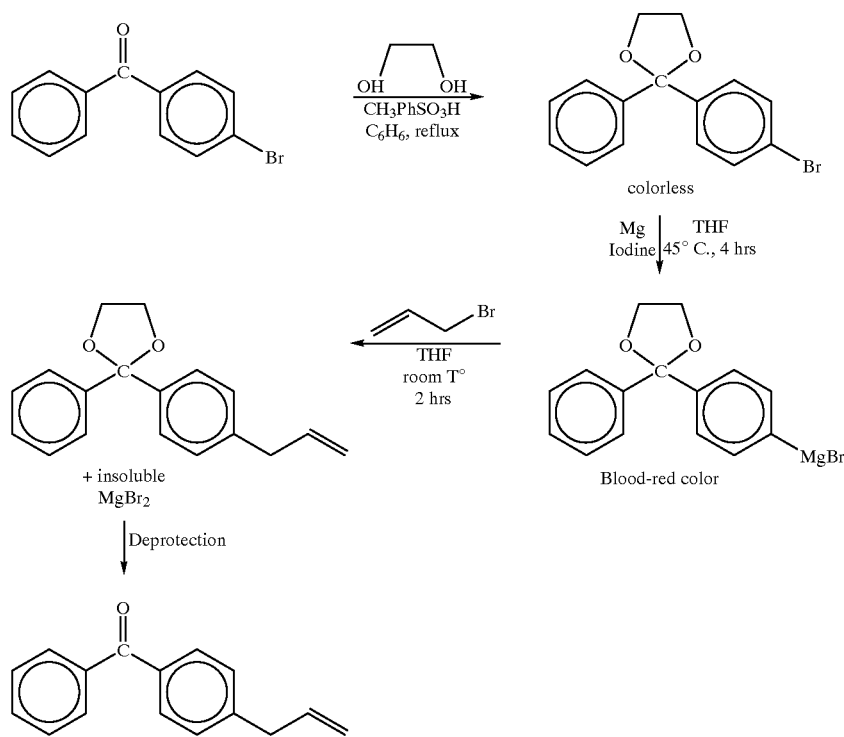

1) Protection of the Carbonyl Functional Group by Synthesis of an Acetal

The first stage consists in protecting the carbonyl functional group of the bromobenzophenone by the formation of a cyclic acetal. This reaction is carried out experimentally in solution in benzene by using a Dean-Stark device in order to remove the water released in the process.

The operating conditions are as follows:

The following are introduced into a 250 ml round-bottomed flask surmounted by a Dean-Stark device and by a condenser:

| 4-Bromobenzophenone | 80.0 g | i.e. 0.306 mol |
|---|---|---|
| Ethylene glycol | 18.8 ml | i.e. 0.337 mol (10% excess) |
| Benzene | 130 ml | |
| p-Toluenesulfonic acid | 100 mg | |

The reaction mixture is heated to 110° C. by means of an oil bath. The theoretical amount of water released in the process in the case of a quantitative yield is 5.15 ml. The reaction is continued for 56 hours. The initially cloudy reaction mixture is clear and exhibits a light yellow coloring. 9.478 g of water were collected in total, although the reaction only releases 5.15 g of it. The difference is attributed to the presence of water in the crude benzene used. The solvent is subsequently evaporated at 60° C. by means of a rotary evaporator. Microdrops of residual water or ethylene glycol seem to be present in the medium.

An additional devolatilization is carried out by using an oil bath, thermostatically controlled at 50° C., coupled to the vacuum of a vane pump.

Finally, the structure of the compound obtained was confirmed by $^1H$ and $^{13}C$ NMR in $CDCl_3$.

However, there remains a small amount of unprotected benzophenone which has to be separated. This is because this compound would result in the formation of undesirable products by coupling with the organomagnesium compound which will be prepared during the following stage.

At this point in the synthesis, the product is a slightly yellowish, viscous oil which is beginning to crystallize. After leaving for a day, the product has completely set solid. 100 ml of ethanol are then added and the product is dissolved therein at a temperature in the region of 50° C. No crystallization is induced during the cooling of the solution. A few crystals of 4-bromobenzophenone are then added and the mixture is placed in a refrigerator for about 30 minutes. This treatment makes it possible to obtain beautiful white crystals in the form of plates. Recrystallization is subsequently carried out according to the usual techniques and the purity of the compound thus obtained is confirmed by NMR.

The samples collected at the end of recrystallization are analyzed by $^1H$ NMR in order to confirm the purity thereof, before mixing them with the top fractions. It turns out that this purity is no longer satisfactory for the final two fractions collected.

The total mass of pure acetal collected after recrystallization is 70.0 g.

The synthetic yield, including recrystallization, calculated with respect to the starting amount of 4-bromobenzophenone charged is thus 74.9%.

2) Synthesis of the Organomacrnesium Compound

This second stage consists in reacting the acetal of 4-bromobenzophenone with magnesium turnings, in order to prepare the intermediate organomagnesium derivative which will subsequently be used during the coupling reaction with allyl bromide.

The operating conditions are as follows:

The reaction is carried out under a slight argon flow in a 250 ml, three-necked, round-bottomed flask equipped with a bulb condenser surmounted by a $CaCl_2$ tube, with a 100 ml dropping funnel and with a Y-shaped fitting equipped with a thermometer and an argon inlet.

The reaction is exothermic; however, when additional heating will be necessary, the latter will be achieved with a water bath thermostatically controlled at 45° C.

| Acetal of 4-BrPh | 20.097 g | dissolved in 40 ml of anhydrous THF (0.0686 mol) |
| --- | --- | --- |
| Mg turnings | 1.71 g | in 10 ml of anhydrous THF (0.0704 mol) |
| Iodine | one crystal | |

In a first step, the reactor is purged with argon for approximately 15 minutes. The magnesium, 10 ml of anhydrous THF and an iodine crystal are introduced. The acetal solution is prepared in an Erlenmeyer flask and decanted into the dropping funnel, and then the latter is mounted on the reactor. The reactor is again purged with argon for a few minutes. Approximately 5 ml of acetal solution are subsequently poured into the reactor, then, without stirring, this mixture is subsequently heated using a hairdryer until the appearance of bubbles at the surface of the magnesium turnings; a slight cloudiness is observed in the reaction medium, followed by the rapid appearance of the blood-red color of the organomagnesium compound formed. Stirring is then started and the acetal solution added dropwise.

As the reaction is exothermic, the rate of addition is adjusted so as to maintain the temperature of the reaction medium in the vicinity of 45° C. If necessary, the thermostatically-controlled water bath can be used.

The total duration of the addition is 90 minutes and then the reaction is further continued under these conditions for an additional 90 minutes. At the end of the reaction, there still remains a small amount of unconsumed magnesium turnings in the medium and the solution thus obtained is blood-red in color.

3) Coupling Reaction

Before carrying out the coupling reaction with allyl bromide, the reaction mixture is allowed to cool to room temperature.

The operating conditions are as follows:

A solution of allyl bromide in THF is prepared in a 100 ml dropping funnel by dissolution of 5.8 ml of the bromide (8.108 g, i.e. 0.0671 mol) in 25 ml of anhydrous THF. The funnel is subsequently mounted on the reactor and the addition is begun dropwise.

The appearance of an insoluble compound in the reaction medium is very quickly observed. The latter is in principle the magnesium bromide which is released during the progression of the reaction. The total duration of the addition is one hour and then the stirring is further continued under the same conditions for an additional hour.

At the end of the reaction, the reaction mixture, which is orangey in color, is diluted with a small amount of THF and then filtration is carried out on a sintered glass in order to separate therefrom the residual magnesium as well as the precipitated salt formed during synthesis. The THF is subsequently evaporated using a rotary evaporator. The residue thus obtained is oily and comprises a not insignificant proportion of an insoluble compound, probably a magnesium bromide residue. The residue is taken up in 250 ml of dichloromethane (clear orangey-yellow solution) and then extraction is carried out successively three times with 50 ml of distilled water.

During the first extraction, the phase separation is not sharp but is composed of an emulsion which is very difficult to break down. A significant amount of the synthesized compound is very probably trapped in this emulsion and has to be recovered. The aqueous and emulsified phases are thus reextracted with a small amount of dichloromethane.

Finally, the organic phase is filtered on a sintered glass of porosity 4 and then drying is carried out over magnesium sulfate before removing the dichloromethane. The orangey residue isolated is characterized by NMR.

15.25 g of crude product are thus obtained.

4. Deprotection Reaction

Several routes for deprotection of the carbonyl are possible. Mention may be made of acid hydrolysis and dioxolane exchange by acid catalysis. It is the latter route which will be used here.

The deprotection reaction was carried out on all the product collected during the two syntheses carried out. (The second synthesis is described below).

| Functionalized acetal | 29.92 g |
|---|---|
| Acetone | 150 ml |
| 95% H$_2$SO$_4$ | 0.05 ml |

The reaction temperature is set by the boiling temperature of the acetone. The total duration of the reaction is 2 hours. The solution, initially orangey-yellow, turns red. The solvent is evaporated using a rotary evaporator and then an additional devolatilization is carried out using a vane pump at a temperature in the vicinity of 45° C. 26.92 g of an opaque brown-colored oil are thus collected.

A small amount of crystalline product was separated using a mixture consisting of 450 ml of ethanol and 50 ml of benzene. After filtration and characterization of the crystals by $^1$H NMR, it turned out that this was 4-bromobenzophenone. The filtrate is then concentrated until only approximately 50 to 100 ml of solution remains and then it is cooled to 0° C. A paste settles out at the bottom of the round-bottomed flask. The crystallization process is repeated but few crystals settle out. 24 g of oil remain.

23.24 g of oil are distilled in a bulb oven under a vacuum of 10$^{-2}$ mmHg in a temperature range from 175 to 250° C. 11.94 g of a slightly yellow oil consisting of two phases are collected. The minor phase is attributed to ethylene glycol which would result from a thermal deprotection, catalyzed by sulfuric acid, of an acetal residue present in the oil.

The distillate is centrifuged in order to separate therefrom the ethylene glycol (30 minutes at 10,000 r/min) and then redistillation is carried out at 185° C. under 10$^{-2}$ mmHg. A small amount of ethylene glycol is again released and the distillate is slightly yellow.

The three fractions (top, middle, tail) are characterized by NMR and then the top and middle fractions are combined (11.02+0.58=11.60 g).

Due to the presence of the ethylene glycol, the whole mixture is taken up in 100 ml of benzene, three spatulafuls of silica gel are added and stirring is carried out with the aim of promoting the adsorption of the ethylene glycol on the silica. After filtration on sintered glass and evaporation of the solvent, analysis by $^1$H NMR shows that the amount of ethylene glycol present has been reduced by half.

2nd Synthesis of 4-allylbenzophenone

The equipment and the operating conditions are similar.
Synthesis of the Organomagnesium Derivative The following is placed in the dropping funnel: Acetal of bromobenzophenone: 20.0 g (0.0683 mol) in 75 ml of anhydrous THF.

The following are placed in the round-bottomed flask:

| Mg turnings | 1.63 g (0.0671 mol) |
|---|---|
| Anhydrous THF | 15 ml |
| one iodine crystal | |

5 to 10 ml of the acetal solution are added and then, without stirring, this mixture is heated until the appearance of a release of gas at the surface of the metal. Stirring is then started and the acetal is slowly added dropwise. The blood-red coloring of the organomagnesium derivative develops virtually instantaneously in the reaction medium.

A thermostatically-controlled water bath is used as additional heating and the rate of addition is adjusted so as to maintain the temperature between 43 and 47° C.

The total duration of the addition is 2 hours, after which there still remains an unconsumed magnesium residue. The reaction is continued under the same conditions for an additional 2 hours.

Coupling Reaction with Allyl Bromide:

An allyl bromide solution is prepared by dilution of 6.0 ml of allyl bromide (0.0692 mol) in 50 ml of anhydrous THF.

After cooling the organomagnesium solution to room temperature, the allyl bromide solution is slowly added dropwise over approximately 2 hours. A precipitate rapidly appears in the reaction medium.

At the end of the reaction, this solution is diluted with a small amount of THF and then filtration is carried out on sintered glass of porosity 4, in order to separate therefrom the insoluble salt as well as the residual magnesium. The filtrate is subsequently evaporated at 50° C. using a rotary evaporator and an orangey-colored pasty residue is isolated which is taken up in approximately 250 ml of dichloromethane and then extracted several times with distilled water. The formation of a very stable emulsified phase is once again observed during the first extraction. The organic phase, which is orangey-yellow in color, is subsequently dried over magnesium sulfate and then the solvent is evaporated.

15.65 g of an orange-colored oil are collected.

Monitoring $^1$H NMR confirms the nature of the compound thus prepared, as well as the presence of impurities which it will be necessary to remove after the stage of deprotection of the carbonyl functional group.

Preparation of 4-(allyloxymethyl)benzophenol [sic]

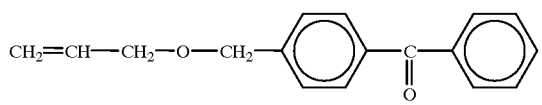

5 g of bromomethylbenzophenone are dissolved in 20 ml of anhydrous THF and the solution obtained is placed in a dropping funnel.

40 ml of THF are introduced into a 500 ml round-bottomed flask equipped with a thermometer, a dropping funnel for the initiator, a dropping funnel for introduction of allyl alcohol and the dropping funnel containing the bromomethylbenzophenone solution. The impurities of the solvent are neutralized with 2 to 3 drops of naphthalene-potassium

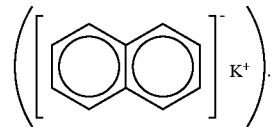

1.2 ml (1.82×10$^{-2}$ mol) of distilled allyl alcohol are then introduced. 20.2 ml of naphthalene-potassium are then added. A white precipitate is formed during the addition. The contents of the dropping funnel containing the bromomethylbenzophenone solution are added. The temperature increases by 5 to 10° C. The precipitate increases in scale and becomes brown-red. The mixture is left stirring for 3 hours. The color of the reaction medium lightens and the temperature decreases. The THF is then driven off and the residue is taken up in benzene. A significant precipitate remains. Washing is carried out with water and the organic phase is filtered. Drying is carried out and then the benzene is removed.

5.69 g of a dark-yellow liquid are collected. The liquid obtained is placed in a sublimator for 5 hours at 100° C. The liquid residue obtained represents 3.40 g (74%). 1.7 g of this residue are distilled in a bulb oven and 0.7 g (57%) of product, distilling at 175° C. under 10⁻² mmHg, is collected.

The remaining 1.7 g are distilled under the same conditions and 0.61 g (41%) of product is collected.

The distillate comprises a portion which is solid at room temperature. The distillate is filtered through a Millipore filter (0.5 μm) and 1.05 g (23%) of the expected product are finally collected, which product corresponds to the formula:

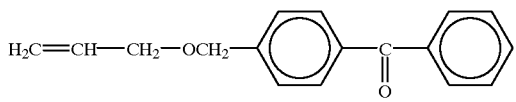

Preparation of 2-hydroxy-1-phenyl-2-methyl-5-hexene-1-one [sic]

(Va)

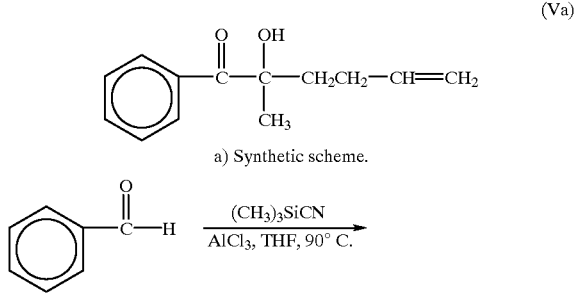

a) Synthetic scheme.

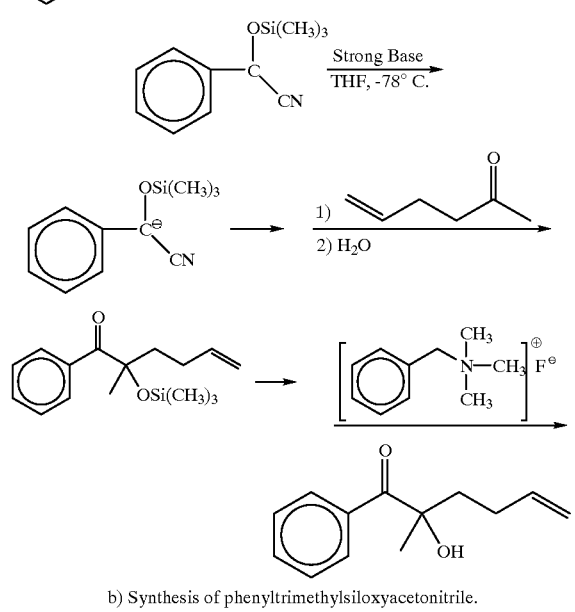

b) Synthesis of phenyltrimethylsiloxyacetonitrile.

5 ml (3.72 g, 37.5 mmol) of trimethylsilyl cyanide (withdrawn using a dry syringe) are added to a solution of 3.98 g (37.5 mmol) of freshly distilled benzaldehyde and 20 mg of AlCl₃ in THF.

The assembly is placed under an inert argon atmosphere and the mixture is heated under reflux to 90° C. After stirring for 10 hours, the solvent is evaporated and the residue is distilled at 80° C. (0.1 mmHg) in a bulb oven.

The expected product is obtained with a yield of 95%.

The structure of the product obtained was confirmed by IR spectrometry (Perkin-Elmer spectrometer) and NMR spectrometry (AC 200 MHz).

c) Synthesis of 2-hydroxy-1-phenyl-2-methyl-5-hexene-1-one [sic]

A solution of tert-butyllithium in hexane (tert-BuLi/hexane) (1.6M, 20 ml, 31.8 mmol) is slowly added, under an argon atmosphere, to a solution of diisopropylamine (3.23 g, 31.9 mmol) in THF (20 ml) at −78° C.

The mixture is maintained at this temperature for 45 minutes. A solution of phenyltrimethylsiloxyacetonitrile (6.54 g, 31.8 mmol) in THF (50 ml) is then added dropwise.

Stirring is maintained for 45 minutes and then a solution of 5-hexene-2-one [sic] (3.26 g, 31.8 mmol) in THF is slowly added to the intense brown solution.

The mixture is kept stirring. After 2 hours at −78° C., the ice bath is removed. When the temperature of the round-bottomed flask reaches 0° C., 300 ml of water are added. The solution obtained is introduced into a separating funnel and extracted with 400 ml of CH₂Cl₂ after shaking several times.

The organic solution recovered is concentrated.

Deprotection of the alcohol group: 5.4 g of benzyltrimethylammonium fluoride, 20 ml of THF and 1 ml of H₂O are added to the organic solution recovered. After stirring for 4 hours, the solution is washed with 4×300 ml of water and then extracted with ether. The ethereal solution is concentrated and distilled in a bulb oven (115° C. at 0.1 mmHg).

The expected product is obtained with a yield of 35%.

The structure of the product was confirmed by IR spectrometry and NMR spectrometry.

Preparation of 1-(o-allylphenyl)-2-trimethylsiloxy-2-methyl-1-butanone.

(Vf)

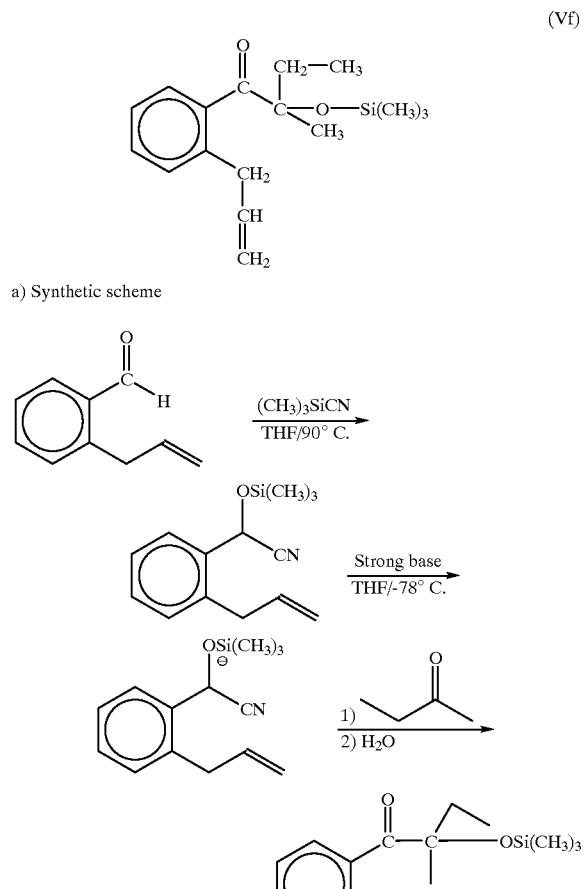

a) Synthetic scheme b) Synthesis of o-allylphenyltrimethylsiloxyacetonitrile.

0.8 ml (600 mg, 6.04 mmol) of trimethylsilyl cyanide is added to a solution of 883 mg of distilled allylbenzaldehyde and 5 mg of anhydrous AlCl₃ in THF.

The assembly is placed under an inert argon atmosphere and the mixture is heated under reflux to 90° C. After stirring for 10 hours, the solvent is evaporated and the residue is distilled at 130° C. (0.1 mmHg) in a bulb oven.

The expected product is obtained with a yield of 85%.

The structure of the product was confirmed by IR spectrometry and NMR spectrometry.

c) Synthesis of 1-(o-allylphenyl)-2-trimethylsiloxy-2-methyl-1-butanone

A solution of tert-BuLi/hexane (1.6M, 2.38 ml, 3.81 mmol) is slowly added, under an argon atmosphere, to a solution of diisopropylamine (395 mg, 3.9 mmol) in THF (20 ml) at −78° C.

The mixture is maintained at this temperature for 15 minutes. A solution of o-allylphenyltrimethylsiloxyacetonitrile (938 mg, 3.81 mmol) in THF (50 ml) is then added dropwise.

Stirring is maintained for 10 minutes and then a solution of butanone (274 mg, 3.81 mmol) in THF is slowly added to the intense brown solution.

The mixture is kept stirring. After 3 hours at −78° C., the ice bath is removed. When the temperature of the round-bottomed flask reaches 0° C., 100 ml of water are added. The solution obtained is introduced into a separating funnel and extracted with 400 ml of $CH_2Cl_2$ after shaking several times.

The organic solution recovered is concentrated and then distilled at 125° C. (0.1 mmHg) in a bulb oven.

The expected product is obtained with a yield of 35%. The structure of the product was confirmed by IR spectrometry and NMR spectrometry.

Preparation of 1-(o-allylphenyl)-2-trimethylsiloxy-2-methyl-5-hexene-1-one [sic]

(Vg)

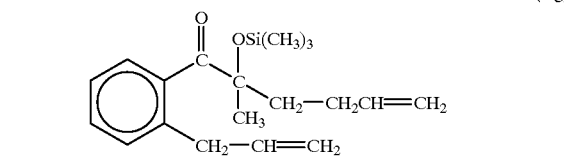

a) Synthetic scheme

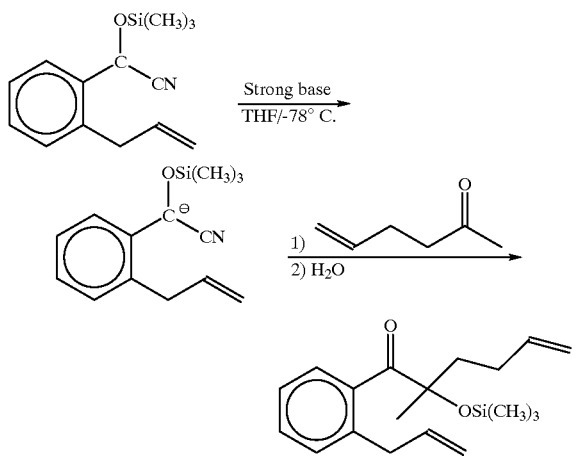

b) Synthesis of 1-(o-allylphenyl)-2-trimethylsiloxy-2-methyl-5-hexene-1-one [sic]

A solution of tert-BuLi/hexane (1.5M, 3.1 ml, 4.7 mmol) is slowly added, under an argon atmosphere, to a solution of diisopropylamine (486 mg, 4.8 mmol) in THF (50 ml) at −78° C.

The mixture is maintained at this temperature for 15 minutes. A solution of o-allylphenyltrimethylsiloxyacetonitrile (1.152 g, 4.7 mmol) in THF (50 ml) is then added dropwise.

Stirring is maintained for 5 minutes and then a solution of 5-hexene-2-one [sic] (471 mg, 4.8 mmol) in THF is slowly added to the intense black solution.

The mixture is kept stirring. After 3 hours at −78° C., the ice bath is removed. When the temperature of the round-bottomed flask reaches 0° C., 400 ml of water are added. The solution obtained is introduced into a separating funnel and extracted with 400 ml of $CH_2Cl_2$ after shaking several times.

The organic solution recovered is concentrated and then distilled at 150° C. (0.1 mmHg) in a bulb oven.

The expected product is obtained with a yield of 45%.

The structure of the product was confirmed by IR spectrometry and NMR spectrometry.

Preparation of 2-trimethylsiloxy-1-phenyl-2-(3-butene)-5-hexene-1-one [sic]

(Vb)

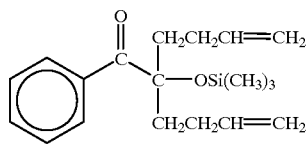

a) Synthetic scheme

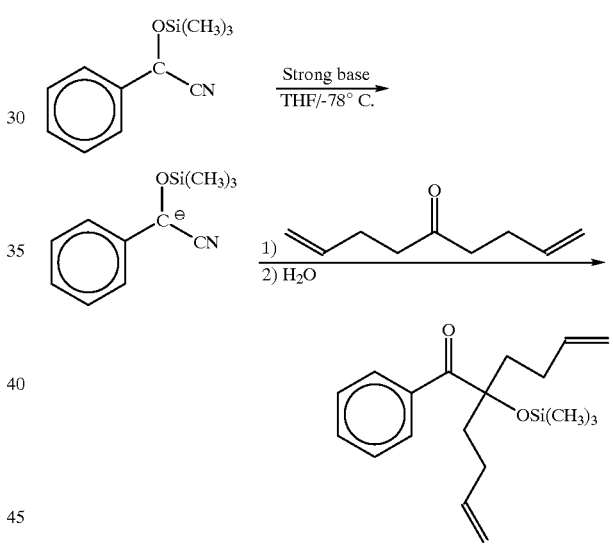

b) Synthesis of 1, 8-nonadiene-5-one [sic]

A solution of tert-BuLi/hexane (1.55M, 13 ml, 20 mmol) is slowly added, under an argon atmosphere, to a solution of diisopropylamine (2.12 g, 21 mmol) in THF (20 ml) at −78° C.

The mixture is maintained at this temperature for 45 minutes. A solution of 5-hexene-2-one [sic] (1.96 g, 20 mmol) in THF (20 ml) is then added dropwise.

Stirring is maintained for 60 minutes and then 1.8 ml of allyl bromide are slowly added to the colorless solution. Stirring is maintained for 12 hours at room temperature.

The resulting red solution is filtered through 2 cm of silica. A yellow solution is then obtained which is concentrated. The residue is distilled in a bulb oven (50° C., 2 mmHg).

The expected product is obtained with a yield of 65%.

The structure was confirmed by IR spectrometry and NMR spectrometry.

c) Synthesis of 2-trimethylsiloxy-1-phenyl-2-(3-butene)-5-hexene-1-one [sic]

A solution of tert-BuLi/hexane (1.55M, 4.1 ml, 6.3 mmol) is slowly added, under an argon atmosphere, to a solution of diisopropylamine (648 g, 6.4 mmol) in THF (20 ml) at −78° C.

The mixture is maintained at this temperature for 15 minutes. A solution of phenyltrimethylsiloxyacetonitrile (1.29 g, 6.3 mmol) in THF (50 ml) is then added dropwise.

Stirring is maintained for 20 minutes and then a solution of 1,8-nonadiene-5-one [sic] (867 mg, 6.3 mmol) in THF is slowly added to the intense brown solution.

The mixture is kept stirring. After 3 hours at −78° C., the ice bath is removed.

When the temperature of the round-bottomed flask reaches 0° C., 200 ml of water are added. The solution obtained is introduced into a separating funnel and extracted with 400 ml of $CH_2Cl_2$ after shaking several times.

The organic solution recovered is concentrated and then distilled at 150° C. (0.1 mmHg) in a bulb oven.

The expected product is obtained with a yield of 30%.

The structure was confirmed by IR spectrometry and NMR spectrometry.

Preparation of ortho-di[2-(o-trimethylsiloxy)-2-(3-butene)-5-hexene-1-one]-1-phenyl [sic]

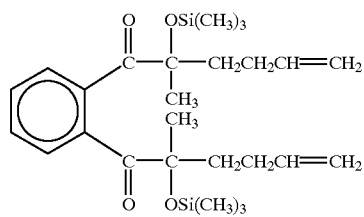

(Vd)

a) Synthetic scheme

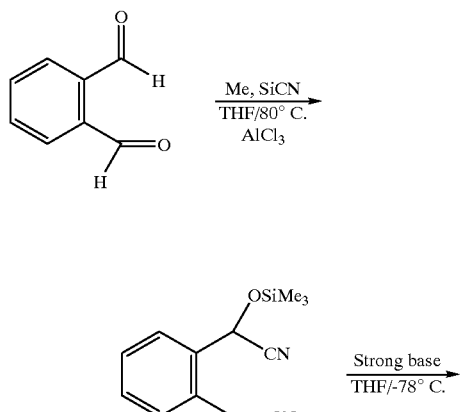

b) Synthesis of ortho-phthalic di(trimethylsiloxyacetonitrile) [sic]

3.565 g (36 mmol) of liquid trimethylsilyl cyanide (withdrawn using a dry syringe) is [sic] added to a solution of 2.41 g (36 mmol) of orthophthaldicarboxyaldehyde [sic] and 20 ml of $AlCl_3$ in THF.

The assembly is placed under an inert argon atmosphere and the mixture is heated under reflux to 900C. After stirring for 10 hours, the solvent is evaporated and the residue is distilled at 175° C. (0.1 mmHg) in a bulb oven.

The expected product is obtained with a yield of 75%.

The structure of the product was confirmed by IR spectrometry and NMR spectrometry.

c) The Continuation of the Synthesis of the Compound (Vd) is Carried Out from Ortho-phthal Di(trimethylsiloxyacetonitrile) [sic] as Above.

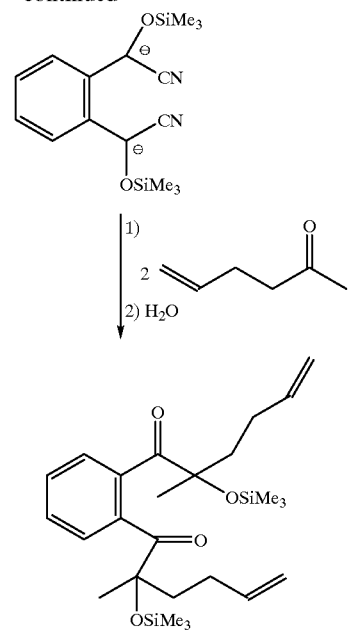

Preparation of a Macrophotoinitiator of the Irgacure® Vinylsilane-polydimethylsiloxane-Irgacure® Vinylsilane Type 0.61 g (8.1×10−4 mol) of a PDMS with silyl endings having a number-average molar mass $M_n$ of approximately 750 and 0.5 g of Irgacure® vinylsilane of formula:

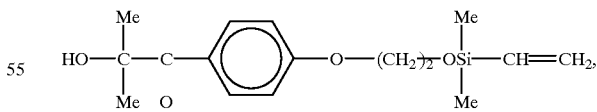

dissolved beforehand in 5 ml of cyclohexane (anionic grade), are placed in a 100 ml round-bottomed flask. 0.12 ml (6.646×10−3 mol) of a solution of $H_2PtCl_6.6H_2O$ in 50 ml of isopropanol is added and the mixture is heated at 70° C. for 8 hours. It is left standing overnight and then filtered through a Millipore® filter (0.45 μm).

The expected product is thus obtained, which product corresponds to the formula:

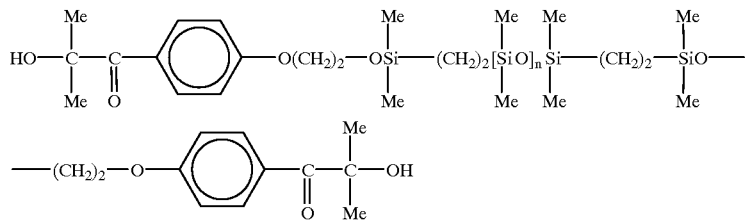

Preparation of a Compound (Va)—Polydimethylsiloxane—Compound (Va) Difunctional Macrophotoinitiator a) Synthetic scheme

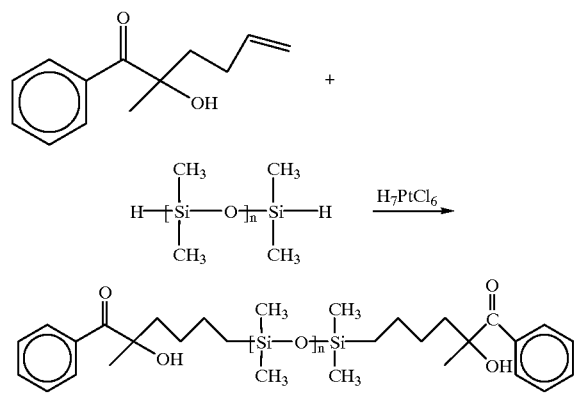

b) Procedure 1.53 g (4.08 mmol) of α,ω-dihydropolydimethylsiloxane (PDMS) and then 833 mg (8.16 mmol) of 2-hydroxy-1-phenyl-2-methyl-5-hexene-1-one [sic] are successively added to a 250 ml three-necked flask. After three vacuum/argon operations, 50 ml of anhydrous toluene are introduced, followed by 2 ml of a solution of $H_2PtCl_6$ in isopropanol (6.646 mmol), and then the mixture is heated to 80° C.

After stirring for 24 hours, the solvent is evaporated. The viscous residue obtained is precipitated from 100 ml of MeOH and dried. In order to remove the traces of catalyst, the filtrate (MeOH) is evaporated and filtered through 2 cm of $SiO_2$ (treated with a cyclohexane solution having 5% of triethylamine, eluent $CH_2Cl_2$), and then dried under vacuum.

Preparation of a Compound (Ve)—Polydimethylsiloxane—Compound (Ve) Difunctional Macrophotoinitiator a) Synthetic scheme

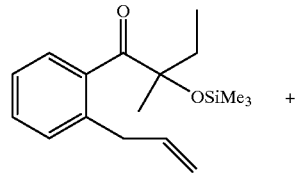

-continued

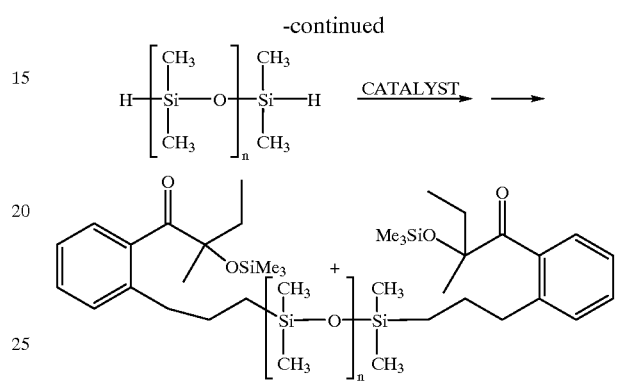

397 mg (0.53 mmol) of α,ω-dihydropolydimethylsiloxane (PDMS) and then 307 mg (1.06 mmol) of 1-(o-allylphenyl)-2-trimethylsiloxy-2-methyl-1-butanone are successively added to a 250 ml three-necked flask. After three vacuum/argon operations, 50 ml of anhydrous toluene are introduced, followed by 1.6 ml of a solution of platinum divinyltetramethyldisiloxane in toluene (0.392 mmol).

After stirring for 24 hours at room temperature, the solvent is evaporated. The viscous residue obtained is precipitated from 150 ml of methanol and dried. In order to remove the traces of catalyst, the filtrate (MeOH) is evaporated and filtered through 2 cm of $SiO_2$ (treated with a cyclohexane solution having 5% of triethylamine, eluent $CH_2Cl_2$), and then dried under vacuum.

Preparation of Multifunctional Macrophotoinitiators

I. From 2-trimethylsiloxy-1-phenyl-2-(3-butene)-5-hexene-1-one [sic]

a) Synthetic scheme

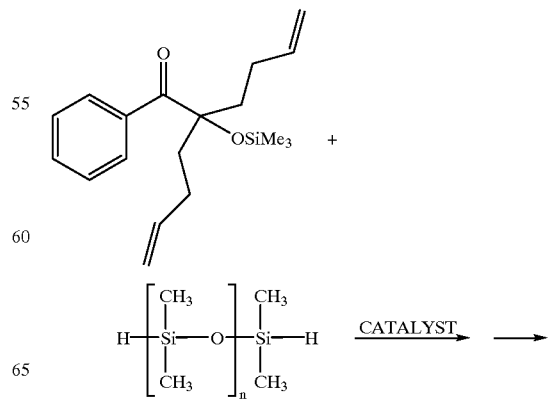

-continued

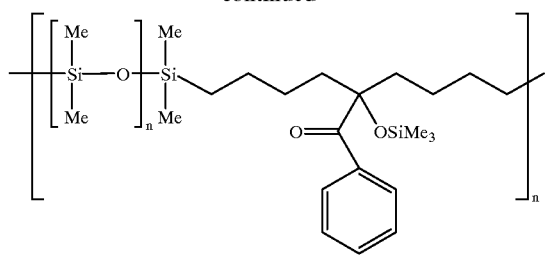

b) Procedure 681 mg (0.9 mmol) of α,ω-dihydropolydimethylsiloxane (PDMS) and then 287 mg (0.9 mmol) of 2-trimethylsiloxy-1-phenyl-2-(3-butene)-5-hexene-1-one [sic] are successively added to a 250 ml three-necked flask.

After three vacuumn/argon operations, 50 ml of anhydrous toluene are introduced, followed by 2.73 ml of a solution of platinum divinyltetramethyldisiloxane in toluene (0.392 mmol/l).

After stirring for 48 hours at room temperature, the solvent is evaporated. The viscous residue obtained is precipitated from 100 ml of methanol. After separation by settling for 3 days, the methanol is removed and the precipitate is dried. The organic phase (MeOH) is evaporated and filtered through 2 cm of $SiO_2$ (treated with a cyclohexane solution having 5% of triethylamine, eluent $CH_2Cl_2$), and then dried under vacuum.

II. From 1-(o-allylphenyl)-2-trimethylsiloxy-2-methyl-5-hexene-1-one [sic]

1.8 g (2.4 mmol) of α,ω-dihydropolydimethylsiloxane (PDMS) and then 760 mg (2.4 mmol) of 1-(o-allylphenyl)-2-trimethylsiloxy-2-methyl-5-hexene-1-one [sic] are successively added to a 250 ml three-necked flask. After three vacuum/argon operations, 50 ml of anhydrous toluene are introduced, followed by 5 ml of a solution of platinum divinyltetramethyldisiloxane in toluene (0.392 mmol/l).

After stirring for 48 hours at room temperature, the solvent is evaporated. The viscous residue obtained is precipitated from 100 ml of methanol. After separation by settling for 4 days, the methanol is removed and the precipitate is dried. The organic phase (MeOH) is evaporated and filtered through 2 cm of $SiO_2$ (treated with a cyclohexane solution having 5% of triethylamine, eluent $CH_2Cl_2$), and then dried under vacuum.

Synthesis of a macrophotoinitiator of formula:

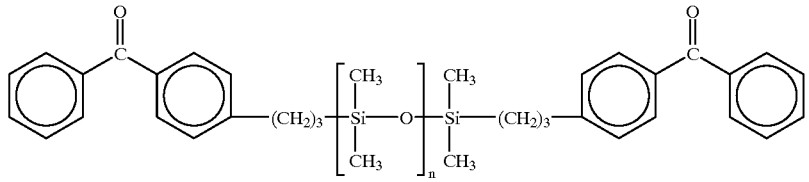

(ALBP-PDMS-ALBP).

5.06 g ($6.75 \times 10^{-3}$ mol) of polydimethylsiloxane oil with silyl endings, Mn=750, and 3.0 g ($1.35 \times 10^{-2}$ mol) of 4-allylbenzophenone are weighed directly in a 250 ml, three-necked, round-bottomed flask equipped with a bulb condenser. After three successive purges with argon, 50 ml of anhydrous benzene and 1.023 ml of a catalyst solution ($H_2PtCl_6 \cdot 6H_2O$–$6.646 \times 10^{-3}$ M solution in isopropanol) are introduced. The mixture is subsequently heated at 70° C. for 8 hours.

At the end of the reaction, the solution is clear. The solvent is evaporated and the presence is then observed of a few solid particles (catalyst) which are removed by filtration through a 0.5 μm Millipore® filter. 8.01 g of the expected product are collected.

Syntheses of a Functionalized Coinitiator and of a Long-chain Coinitiator

A. Synthesis of 4-dimethylvinylsilane-N, N-dimethyl-aniline [sic]:

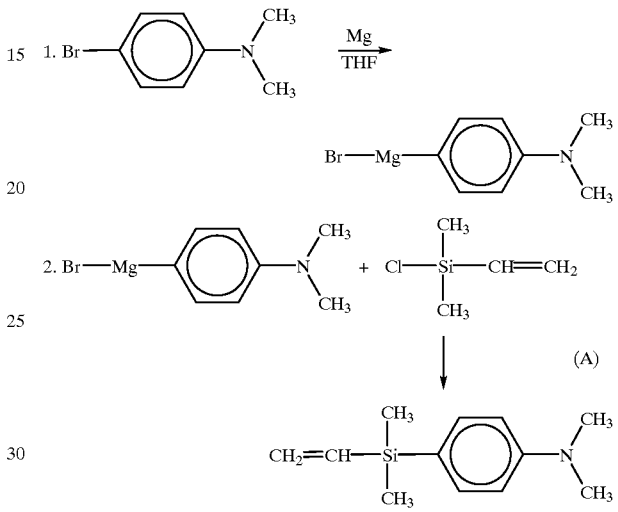

Procedure:

All the materials must be purified before beginning the synthesis. The THF is distilled under argon, over sodium wire, at atmospheric pressure. The 4-bromo-N,N-dimethylaniline (Aldrich) is conditioned under argon. The chlorodircethylvinylsilane (Aldrich) is distilled at atmospheric pressure under a slight argon flow (bp=81° C.). A solution of anhydrous THF (66 ml, ⅔ of the total volume of THF in the reaction medium) and of 4-bromo-N,N-dimethylvinylaniline (m=20.01 g, n=0.1 mol) is subsequently prepared in a dropping funnel under argon.

2.673 g (0.11 mol) of magnesium and an iodine crystal are introduced into a reactor equipped with a mechanical stirrer, a reflux condenser and a thermometer. The assembly is then conditioned under argon. 30 ml of THF are introduced under an argon flow. The solution then becomes brown-yellow. At most 1/10 of the bromine/THF [sic] solution is then added under argon. After reacting for ½ hour, the solution becomes colorless-cloudy and then, after ¾ hour, purple. A slight warming is then observed and reflux occurs.

The brominated [sic] solution is subsequently added dropwise under argon. At the end of the addition, the reaction medium is heated at 50° C. for two hours. The temperature of the solution is allowed to return to room temperature.

13.81 ml (0.1 mol) of silane chloride are subsequently added dropwise. A warming of the reaction medium is observed. At the end of the addition, stirring is continued for 15 minutes and then 8 ml of water are added. A white emulsion is produced and refluxing occurs. After having allowed the temperature of the reaction medium to return to room temperature, 100 ml of $H_2O$ and 100 ml of ether are added. The solution is filtered. The organic phase is separated from the aqueous phase and washed with a saturated $NaCO_3$ solution. The solution, which is yellow in color, is dried over $MgSO_4$ and the solvents are driven off.

Crude yield=91%

Crude mass=18.7 g

The crude product is distilled under vacuum, bp $_{0.1}$=79° C., yield=50%.

B. Condensation of 4-dimethylvinylsilane-N,N-dimethyl-aniline [sic] with a PDMS

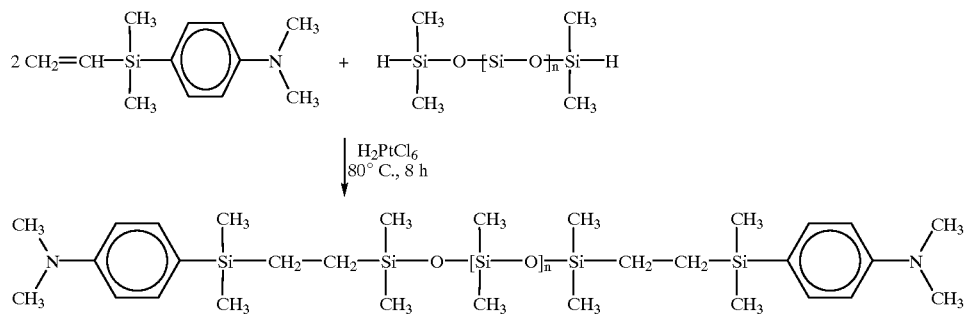

Procedure:

1 g (0.0049 mol) of the product obtained in the preceding stage and then 1.8293 g (0.0024 mol) of PDMS (Mn=750) are introduced into a three-necked flask, conditioned under argon, equipped with a magnetic stirrer. Dry toluene, 50% by mass, and 3.3 ml of the $H_2PtCl_6$ catalyst ($5 \times 10^{-4}$ mol/SiH functional group) are subsequently added. The reaction medium is heated at 80° C. for 8 hours. The solution becomes black and refluxing occurs. At the end of the reaction, the temperature of the reaction medium returns to room temperature. A portion of the solution is then precipitated from a minimum amount of ethanol and a portion of the crude is characterized.

Quantitative determination of the residual hydrosilane functional groups of the polymer shows that the functionalization is virtually quantitative.

Preparation of the Hydrophilic Ppolymers According to the Invention

The polymeric products which are hydrophilic to the core and transparent, according to the invention, are prepared according to a process comprising the following stages:

a) The material based on crosslinked silicone olymer comprising the photoinitiator, for example PDMS, obtained above is diffused and swollen in a solution comprising a photopolymerizable hydrophilic monomer, a solvent for swelling the material based on crosslinked silicone polymer and preferably a crosslinking agent; and b) the hydrophilic monomer is polymerized by irradiation and optionally the crosslinking agent is polymerized, in order to obtain the final hydrophilic polymeric product.

There exists no specific limitation with respect to the hydrophilic monomer to be used, provided that the latter is soluble in a solvent for swelling the material based on silicone polymer and that it is, furthermore, photopolymerizable.

Use may be made, in particular, of acrylic or methacrylic acid or hydroxyalkyl (meth)acrylates, such as hydroxyethyl methacrylate (HEMA).

Some monomers which make it possible to avoid lipid or protein deposits can be incorporated, such as, for example, glyceryl methacrylate and (meth)acrylate derivatives of glucuronic or galacturonic acid.

In the swelling solution, the

[hydrophilic monomer]/[solvent]

ratio is preferably less than 0.5 and better still less than 0.2.

The solvent used must be able, at least partially, to dissolve the hydrophilic monomer and be an agent for swelling the silicone material. It is preferably low in volatility. Use will be made, for example, of toluene, cyclohexane, tetrahydrofuran, dodecane or a fluorinated solvent.

The crosslinking agent used must, like the hydrophilic monomer, be photopolymerizable and at least partially soluble in the solvent. Use will be made, for example, of ethylene glycol dimethacrylate (EGDMA).

Two preferred embodiments of the process for the preparation of the hydrophilic products, according to the invention, will now be described:

The first process consists in carrying out the photopolymerization stage b) by compressing the disk of material based on crosslinked silicone polymer in a mold which is transparent to UV radiation and which corresponds to the irradiation region of the photoinitiator.

The reverse diffusion reactions of the swelling solution are then limited.

The second process, which is preferably used, in particular for industrial exploitation, consists in irradiating the swollen material while the latter is immersed in the swelling solution.

It is found, in this case, that polymeric products are obtained with a higher level of hydrophilicity than in the process of the prior art where the photoinitiator is present in the swelling solution.

The hydrophilic polymeric products obtained have different final structures which depend in particular on the nature of the photoinitiator group used and, incidentally, whether the photoinitiator groups are or are not attached to silicon atoms of the crosslinked silicone polymer of the matrix via covalent bonds and whether the photoinitiating entity formed during the photopolymerization remains attached or not to the silicone polymer of the matrix.

When the photoinitiating entity remains attached chemically to the silicone polymer of the matrix, the polymer resulting from the photopolymerization of the hydrophilic monomer is, at least partially, grafted to this silicone polymer.

In general, when the photoinitiator groups are not grafted to the silicone polymer of the matrix or when the photoinitiating entities created during the photopolymerization are free, the hydrophilic polymeric products obtained exhibit a structure mainly and sometimes even solely of IPN type.

Thus, when Irgacure® vinylsilane is used as photoinitiator, this photoinitiator is grafted via the vinyl functional groups to the crosslinked PDMS of the matrix during the crosslinking. During the irradiation, the photoinitiator forms a $C(Me_2)OH$ free radical while the photoinitiating entity

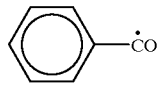

remains attached to the crosslinked PDMS of the matrix. For this reason, the hydrophilic polymer resulting from the photopolymerization of the hydrophilic monomer, for example acrylic acid, will be, at least partially, grafted to the crosslinked PDMS of the matrix via the photoinitiating entities grafted to this crosslinked PDMS.

The invention thus also relates to a hydrophilic polymeric product obtained by the process described above, in which photoinitiator groups are attached via covalent bonds to Si atoms of the crosslinked silicone polymer of the matrix and the hydrophilic polymer obtained by photopolymerization of the photopolymerizable hydrophilic monomer is, at least partially, grafted to the crosslinked silicone polymer of the matrix.

The hydrophilic polymeric products are particularly suited to the manufacture of ophthalmic items, such as contact lenses.

EXAMPLES

I—Preparation of Disks or [sic] Material Based on Crosslinked Silicone Polymers Incorporating the Photoinitiator.

Silicone disks (incorporating the photoinitiator) with a diameter of 14 mm and a thickness of 0.2 mm are prepared.

The photoinitiator is added to the mixture of siloxane prepolymers (10% by weight oil A+1% by eight oil B) mentioned above.

The mixture is degassed and poured into
either polyamide molds (PAm)
or polypropylene molds (PPm).

The molds are subsequently heated under pressure for 8 hours at 64° C. and 15 hours at 83° C.

The disks obtained are transparent, flexible and elastic.

The disks obtained are subsequently extracted with cyclohexane, so as to remove the unreacted constituents.

The disks, after extraction, are subsequently characterized by confirming, by a UV spectrum of the sample, the presence of the absorption bands characteristic of the photoinitiator.

In all cases, it was found that the photoinitiator was thoroughly immobilized within the crosslinked silicone polymer matrix of the disks.

The following photoinitiators were tested:
Darocure® methacrylate
Ivs
IVS-PDMS-IVS
ALBP
ALOBP.

II—Preparation of the Hydrophilic Polymeric Products
II.1—Process by Molding

The disks obtained above are swollen in a solution containing:
the hydrophilic monomer
the mixed solvent for the hydrophilic monomer and the silicone material
the crosslinking agent EGDMA.

When the diffusion equilibrium is reached, the sample is dried and placed between two quartz mold parts (in order to avoid the reverse diffusion of solvent and monomer) covered with a polyethylene film (in order to avoid adhesion of the hydrophilic polymer, in particular poly(acrylic acid), to the glass).

The irradiation source is a mercury vapor lamp (100 W) maintained at a distance of 12 to 13 cm.

Continuous rotation of the sample makes it possible to irradiate each face of the disk alternately.

Irradiation is maintained for 15 minutes.

After irradiation, the sample is dried in order to remove the solvent. It is then extracted with water in order to remove the monomer and oligomers.

The sample is then hydrated in distilled water until equilibrium is reached.

II.2—Vessel Process.

The disk made of silicone material is introduced into a quartz vessel with a thickness of 0.4 mm containing the hydrophilic monomer, the crosslinking agent and the solvent.

Irradiation is carried out after swelling and after the diffusion equilibrium has been obtained.

Irradiation lasts 30 minutes. The irradiation source-sample distance is from 12 to 13 cm.

EXAMPLES 1 to 16

Quartz molds - acrylic acid hydrophilic monomer

Swelling solution:
0.294 g of acrylic acid (AA);
0.006 g of ethylene glycol dimethacrylate (EGDMA);
1.7 g of cyclohexane;
0.007 g of EDMAB coinitiator.

ratio $\dfrac{[\text{acrylic acid}]}{[\text{cyclohexane}]} = \dfrac{85}{15}$

| Ex. No. | Material based on crosslinked silicone polymer | Mold | % PAA | % H$_2$O |
|---|---|---|---|---|
| 1 | PDMS + 1% by weight ALOBP | PAm | 25 | 38 |
| 2 | PDMS + 1% by weight ALOBP | PAm | 23 | 32 |
| 3 | PDMS + 1% by weight ALOBP | PAm | 26 | 49 |
| 4 | PDMS + 1% by weight ALOBP | PAm | 25 | 40 |
| 5 | PDMS + 1% by weight ALOBP | PAm | 20 | 43 |
| 6 | PDMS + 0.5% by weight ALBP | PAm | 5 | 22 |
| 7 | PDMS + 1% by weight ALBP | PAm | 29 | 40 |
| 8 | PDMS + 1% by weight ALBP | PPm | 26 | 46 |
| 9 | PDMS + 1% by weight ALBP | PPm | 17 | 31 |
| 10 | PDMS + 3% by weight ALBP | PAm | 21 | 34 |

-continued

Vessel - acrylic acid hydrophilic monomer

Swelling solution:
0.294 g of acrylic acid (AA);
0.006 g of ethylene glycol dimethacrylate (EGDMA);
1.7 g of cyclohexane;
0.015 g of EDMAB coinitiator.

$$\text{ratio} \frac{[\text{acrylic acid}]}{[\text{cyclohexane}]} = \frac{85}{15}$$

| Ex. No. | Material based on cross-linked silicone polymer | Mold | % PAA | % H$_2$O |
|---|---|---|---|---|
| 11 | PDMS + 1% by weight ALOBP | PAm | 42 | 58 |
| 12 | PDMS + 1% by weight ALOBP | PAm | 22 | 47 |
| 13 | PDMS + 1% by weight ALOBP | PAm | 29 | 57 |
| 14 | PDMS + 1% by weight ALOBP | PAm | 44 | 47 |
| 15 | PDMS + 1% by weight ALOBP | PAm | 25 | 31 |
| 16 | PDMS + 1% by weight ALBP | PPm | 33 | 40 |

EXAMPLES 17 to 26

TESTS WITH DIFFERENT HYDROPHILIC MONOMERS

The swelling solution is identical to that used Examples 1 to 16.

a) Photopolymerization in a quartz mold-Material based on crosslinked silicone polymer: PDMS+1% ALOBP.

| Ex. No. | Hydrophilic monomer | Mold | % polymer | % H$_2$O | % swelling |
|---|---|---|---|---|---|
| 17 | HEMA | PPm | 5 | 10 | 51 |
| 18 | HEMA | PAm | 9 | 19 | 47 |
| 19 | Methacrylic acid (MA) | PPm | 31 | 30 | 71 |
| 20 | Methacrylic acid (MA) | PAm | 24 | 22 | 64 |
| 21 | AA | PPm | 31 | 37 | 74 |
| 22 | AA | PAm | 22 | 29 | 61 | b) Photopolymerization in vessels—Hydrophilic monomer HEMA in solution in toluene.

| Ex. No. | Hydrophilic monomer | Material based on crosslinked silicone polymer | Mold | % polymer | % H$_2$O |
|---|---|---|---|---|---|
| 23* | HEMA | PDMS + 3% ALBP | PPm | 25 | 12 |
| 24** | HEMA | PDMS + 3% ALBP | PPm | 60 | 25 |
| 25* | HEMA | PDMS + 1% ALBP | PPm | 12 | 7 |
| 26 | HEMA | PDMS + 1% ALBP | PPm | 57 | 21 |

*Flexible and transparent samples.
**Transparent and slightly stiff.

The mechanical properties (stress and elongation) of hydrophilic polymeric products with an IPN network of the prior art were measured with hydrophilic polymeric products according to the invention.

The results are shown below:

| | Network 1 | Network 2 | Mold | Stress MPa | Elongation % |
|---|---|---|---|---|---|
| Prior art product | PDMS | PAA | PPm | 0.45 ± 0.26 | 62 ± 39 |
| Product according to the invention | PDMS + 1% ALOBP | PAA | PPm | 0.73 ± 0.31 | 95 ± 66 |
| Product according to the invention | PDMS + 1% ALOBP | PAA | PAm | 2.12 ± 0.13 | 111 ± 11 |
| Product according to the invention | PDMS + 1% ALOBP | PMA | PPm | 2.51 ± 0.33 | 163 ± 29 |

EXAMPLES 27 to 30

Tests with the Coinitiator Chemically Attached within the Silicone Matrix

Chemical formula of the coinitiator:

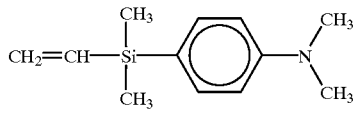

4-Dimethylvinylsilane-N,N-dimethylaniline [sic]
MM=205
U.V. 269 nm

With the coinitiator chemically attached, the initiating mechanism will be different. In this case, the radical responsible for the initiating is the radical resulting from the amine and thus the PAA chains which will be formed will be attached to the PDMS matrix.

a) PDMS disks (PP mold) in which the polymerizable coinitiator (1%) and ALBP (1%) have been incorporated
Swelling solution: acrylic acid+crosslinking agent+cyclohexane Polymerization in a quartz mold for 15 minutes (under N$_2$).
Results:

| PDMS-Coinit-ALBP | Swelling in the solution % | % PAA | % H$_2$O |
|---|---|---|---|
| Example 27 | 71 | 27 | 28 |
| Example 28 | 75 | 30 | 30 |

After photopolymerization the samples remain transparent and relatively flexible.

The percentage of polymer was obtained by initially determining the mass m of the disks made of material based on crosslinked silicone polymer before the photopolymerization stage.

After the photopolymerization, the sample is extracted in chloroform and then dried and its mass m' determined. It is possible, from the values of m and m' to calculate the percentage of polymer (for example PAA) incorporated:

$$\% \text{ H}_2\text{O} = \frac{m_H - m''}{m_H} \times 100.$$

However, a certain amount of polymer may have polymerized at the surface of the disk. This polymer can be removed by extraction in an appropriate medium, for example distilled water in the case of PAA. After dehydration, the new mass m" of the disk is determined, and the true amount of polymer incorporated and the amount of polymer polymerized at the surface which has been extracted.

The degrees of hydration are determined after swelling in distilled water or physiological serum (hydrated mass=$m_H$) from the relationship:

$$\% \text{ polymer} = \frac{m' - m}{m'} \times 100 \text{ [sic]}$$

What is claimed is:

1. A process for the manufacture of a hydrophilic polymeric product, comprising:
    a) causing a material comprising a crosslinked silicone polymer matrix and photoinitiator groups dispersed and immobilized within the polymer matrix to swell in a swelling solution comprising a solvent for swelling the crosslinked silicone polymer of the matrix of the material, a photopolymerizable hydrophilic monomer and optionally:
        1) a crosslinking agent; and
        2) a proton- or electron-donating coinitiator compound, when the material comprises photoactivable photoinitiator groups and does not comprise proton- or electron-donating coinitiator groups;
    b) causing the photopolymerizable hydrophilic monomer to diffuse into the swollen material; and
    c) polymerizing, by irradiation, the photopolymerizable hydrophilic monomer.

2. The process of claim 1, wherein the photoinitiator groups are attached to the crosslinked silicone polymer constituting the matrix via covalent Si—C bonds.

3. The process of claim 1, wherein the photoinitiator groups are grafted to a long-chain compound dispersed and physically immobilized within the matrix.

4. The process of claim 3, wherein the long-chain compound is a polydimethysilane (PDMS).

5. The process according to claim 1 wherein the photoinitiator groups are photocleavable groups.

6. The process according to claim 1, wherein the photoinitiator groups are photoactivable groups.

7. The process of claim 6, wherein the material further comprises proton- or electron-donating coinitiator groups.

8. The process of claim 7, wherein the coinitiator groups are linked chemically to the crosslinked silicone polymer of the matrix.

9. The process of claim 7, wherein the coinitiator groups are linked by a long-chain compound dispersed and immobilized within the matrix.

10. The process according to claim 1 wherein the crosslinked silicone polymer of the matrix is a polydimethysiloxane.

11. The process of claim 10, wherein the crosslinked silicone polymer of the matrix results from the thermal polymerization of a mixture of an oil of a polysiloxane monomer or oligomer carrying Si-vinyl groups and of an oil of a polysiloxane monomer or oligomer carrying Si-H groups in the presence of a hydrosilylation catalyst.

12. The process of claim 11, wherein the mixture of the polysiloxane oils comprises 0.8 to 1.9 Si—H bonds per 1 Si-vinyl bond.

13. The process according to claim 1 wherein the photopolymerizable hydrophilic monomer is acrylic acid, methacrylic acid, hydroxyalkyl (meth)acrylates, or a combination thereof.

14. The process according to claim 1 wherein the hydrophilic monomer/solvent ratio is less than 0.5.

15. The process according to claim 1 wherein the hydrophilic monomer/solvent ratio is less than 0.2.

16. The process according to claim 1 wherein the solvent is toluene, cyclohexane, dodecane, tetrahydrofuran, fluorinated solvents, or a combination thereof.

17. The process according to claim 1 wherein the polymerization of the swollen material is carried out outside the swelling solution.

18. The process according to claim 1, wherein the polymerization of the swollen material is carried out with the material immersed in the swelling solution.

19. Hydrophilic polymeric product obtained by the process according to claim 1, in which the photoinitiator groups are attached through covalent bonds to silicon atoms of the crosslinked silicone polymer of the matrix, and the hydrophilic polymer obtained after photopolymerization of the polymerizable hydrophilic monomer is, at least partially, grafted to the crosslinked silicone polymer of the matrix.

* * * * *